(12) United States Patent
Dhuper et al.

(10) Patent No.: US 7,841,341 B2
(45) Date of Patent: *Nov. 30, 2010

(54) INTERFACE ACCESSORY FOR USE WITH AN AEROSOL INHALATION SYSTEM

(75) Inventors: Sunil Kumar Dhuper, Old Westbury, NY (US); Herbert Fred D'Alo, Madison, CT (US)

(73) Assignee: Aeon Research and Technology, Inc., Hewlett, NY (US)

( * ) Notice: Subject to any disclaimer, the term of this patent is extended or adjusted under 35 U.S.C. 154(b) by 1014 days.

This patent is subject to a terminal disclaimer.

(21) Appl. No.: 11/414,737

(22) Filed: Apr. 27, 2006

(65) Prior Publication Data

US 2006/0260607 A1    Nov. 23, 2006

Related U.S. Application Data

(63) Continuation-in-part of application No. 11/121,688, filed on May 3, 2005, now Pat. No. 7,445,006.

(51) Int. Cl.
*A61M 16/00* (2006.01)
*A61M 15/00* (2006.01)

(52) U.S. Cl. .................. 128/203.15; 128/203.12; 128/200.24

(58) Field of Classification Search ............ 128/200.24, 128/203.12, 203.25, 204.18, 205.25, 206.12, 128/206.21; 239/338
See application file for complete search history.

(56) References Cited

U.S. PATENT DOCUMENTS

| | | | |
|---|---|---|---|
| 3,057,347 A | 10/1962 | McGee | |
| 3,903,884 A | 9/1975 | Huston et al. | |
| 4,210,155 A | 7/1980 | Grimes | |
| 4,463,755 A | 8/1984 | Suzuki | |
| 4,470,412 A | 9/1984 | Nowacki et al. | |
| 4,637,528 A | 1/1987 | Wachinski et al. | |
| 4,641,644 A | 2/1987 | Andersson et al. | |
| 4,649,912 A | 3/1987 | Collins | |
| 4,823,784 A | 4/1989 | Bordoni et al. | |
| 4,951,661 A | 8/1990 | Sladek | |
| 4,953,545 A | 9/1990 | McCarty | |
| 5,012,803 A | 5/1991 | Foley et al. | |
| 5,020,530 A | 6/1991 | Miller | |
| 5,263,485 A | 11/1993 | Hickey | |
| 5,277,175 A | 1/1994 | Riggs et al. | |
| 5,287,849 A | 2/1994 | Piper et al. | |
| 5,349,946 A | 9/1994 | McComb | |
| 5,385,140 A | 1/1995 | Smith | |
| 5,388,571 A | 2/1995 | Roberts et al. | |

(Continued)

*Primary Examiner*—Justine R Yu
*Assistant Examiner*—Annette F Dixon
(74) *Attorney, Agent, or Firm*—Leason Ellis LLP

(57) ABSTRACT

According to one aspect of the present invention, an accessory for an aerosol inhalation system includes a main conduit body having an outlet end for placement close to a mouth of a patient, and first and second leg conduits that are in fluid communication with the main conduit body. The accessory further includes a holding chamber having a first compartment and a second compartment separated from the first compartment, with the first compartment being sealingly and fluidly coupled to the one port associated with the first leg conduit and the second compartment is sealingly and fluidly coupled to a port associated with the second leg conduit. An arrangement of valves is provided for directing fluid along prescribed flow paths depending on whether the patient inhales or exhales.

27 Claims, 5 Drawing Sheets

U.S. PATENT DOCUMENTS

| | | | |
|---|---|---|---|
| 5,479,920 A | 1/1996 | Piper et al. | |
| 5,482,031 A | 1/1996 | Lambert | |
| 5,546,930 A | 8/1996 | Wikefeldt | |
| 5,586,551 A | 12/1996 | Hilliard | |
| 5,613,489 A | 3/1997 | Miller et al. | |
| 5,617,844 A | 4/1997 | King | |
| 5,640,951 A | 6/1997 | Huddart et al. | |
| 5,727,542 A | 3/1998 | King | |
| 5,738,087 A | 4/1998 | King | |
| 5,752,502 A | 5/1998 | King | |
| 5,791,340 A | 8/1998 | Schleufe et al. | |
| 5,813,423 A | 9/1998 | Kirchgeorg | |
| 5,848,587 A | 12/1998 | King | |
| 5,865,172 A | 2/1999 | Butler et al. | |
| 6,039,042 A | 3/2000 | Sladek | |
| 6,041,777 A | 3/2000 | Faithfull et al. | |
| 6,078,730 A | 6/2000 | Huddart et al. | |
| 6,116,233 A | 9/2000 | Denyer et al. | |
| 6,192,884 B1 | 2/2001 | Vann et al. | |
| 6,340,023 B2* | 1/2002 | Elkins | 128/200.21 |
| 6,363,932 B1 | 4/2002 | Forchione et al. | |
| 6,390,090 B1 | 5/2002 | Piper | |
| 6,427,685 B1 | 8/2002 | Ray | |
| 6,450,163 B1 | 9/2002 | Blacker et al. | |
| 6,494,202 B2 | 12/2002 | Farmer | |
| 6,550,476 B1 | 4/2003 | Ryder | |
| 6,622,725 B1 | 9/2003 | Fisher et al. | |
| 6,748,945 B2 | 6/2004 | Grychowski et al. | |
| 6,772,754 B1 | 8/2004 | Mendenhall | |
| 6,776,160 B2 | 8/2004 | Wang | |
| 6,799,423 B2 | 10/2004 | Piekarski | |
| 6,929,003 B2 | 8/2005 | Blacker et al. | |
| 6,976,488 B2 | 12/2005 | Halperin | |
| 6,994,083 B2 | 2/2006 | Foley et al. | |
| 7,036,500 B2 | 5/2006 | Niles et al. | |
| 7,080,643 B2 | 7/2006 | Grychowski et al. | |
| 7,131,439 B2 | 11/2006 | Blacker et al. | |
| 7,191,776 B2 | 3/2007 | Niles et al. | |
| 7,290,541 B2 | 11/2007 | Ivri et al. | |
| 7,445,006 B2 | 11/2008 | Dhuper et al. | |
| 2002/0017302 A1 | 2/2002 | Fukunaga et al. | |
| 2002/0121275 A1 | 9/2002 | Johnson et al. | |
| 2002/0129814 A1 | 9/2002 | Sladek | |
| 2003/0010336 A1 | 1/2003 | Vito | |
| 2003/0209246 A1 | 11/2003 | Schroeder et al. | |
| 2004/0011364 A1 | 1/2004 | Dhuper et al. | |
| 2004/0024372 A1 | 2/2004 | Grogan | |
| 2004/0084048 A1 | 5/2004 | Stenzler et al. | |
| 2004/0123974 A1 | 7/2004 | Marler et al. | |
| 2004/0226563 A1 | 11/2004 | Xu et al. | |
| 2004/0234610 A1* | 11/2004 | Hall et al. | 424/489 |
| 2005/0028811 A1 | 2/2005 | Nelson et al. | |
| 2005/0092325 A1 | 5/2005 | Dionne | |
| 2005/0247313 A1* | 11/2005 | Niles et al. | 128/203.16 |
| 2006/0231090 A1 | 10/2006 | King | |
| 2006/0231091 A1* | 10/2006 | Camarillo | 128/200.21 |
| 2006/0260607 A1 | 11/2006 | Dhuper et al. | |
| 2007/0062531 A1 | 3/2007 | Fisher | |
| 2008/0087280 A1 | 4/2008 | Dhuper et al. | |

* cited by examiner

INTERFACE ACCESSORY FOR USE WITH AN AEROSOL INHALATION SYSTEM

CROSS-REFERENCE TO RELATED APPLICATION

The present application is a continuation-in part of U.S. patent application Ser. No. 11/121,688, filed May 3, 2005, (now U.S. Pat. No. 7,445,006, issued on Nov. 4, 2008) which is hereby incorporated by reference in its entirety.

TECHNICAL FIELD

The present invention relates to inhalation equipment and more particularly, relates to aerosol inhalation systems including an interface (accessory) for use in the system between a conventional part of the inhalation equipment, such as a generator, and the patient to provide in a number of applications a completely closed system that ensures that the medication delivered to the patient has a fixed concentration over time.

BACKGROUND

Aerosol inhalation equipment is commonly used as a means to deliver medication in an aerosolized form to a patient. Aerosolized medication is typically used to treat patients with respiratory conditions, such as asthma or chronic obstructive pulmonary disease (COPD). For example, inhalation equipment is a common means for delivering medication to counter certain aliments of a patient population, including reactive airway disease, asthma, cystic fibrosis, etc.

It is generally accepted that effective administration of medication as aerosol depends on the delivery system and its position in relation to the patient. Aerosol particle deposition is influenced by particle size, ventilatory pattern, and airway architecture and effective medication response is also influenced by the dose of the medication used.

An aerosol delivery system includes three principal elements, namely a generator, a power source, and an interface. Generators include small volume nebulizers (SVN), large volume nebulizers (LVN), metered dose inhalers (MDI), and dry powder inhalers (DPI). The power source is the mechanism by which the generator operates or is actuated and includes compressed gas for SVN and LVN and self-contained propellants for MDI. The interface is the conduit between the generator and the patient and includes spacer devices/accessory devices with mouthpieces or face masks. Depending on the patient's age (ability) and coordination, various interfaces are used in conjunction with SVN and MDI in order to optimize drug delivery.

A SVN is a jet nebulizer that is powered by a compressed gas source. The medication is displaced up a capillary tube from the nebulizer's reservoir and is dispersed continuously as aerosolized particles. The aerosolized particles are spontaneously inhaled by the patient or delivered in conjunction with positive-pressure breaths. Typically, for patients greater than 3 years who are spontaneously breathing without an artificial airway and are able to cooperate, a mouthpiece with an extension reservoir should be used. For patients unable to negotiate a mouthpiece, typically children under 3 years, a face mask should be used.

An MDI is essentially a pressurized canister that contains a medication and propellant. Actuation of the MDI results in the ejection of one dose of medication as aerosolized particles, which can be spontaneously inhaled by the patient or delivered in conjunction with positive-pressure breaths. A spacer device/accessory device should be used with an MDI. A spacer device enhances delivery by decreasing the velocity of the particles and reducing the number of large particles. A spacer device with a one-way valve, i.e., holding chamber, eliminates the need for the patient to coordinate actuation and inhalation and optimizes drug delivery. A spacer device without valves requires coordination between inhalation and actuation. The MDI with spacer device and face mask is appropriate for patients, typically less than 3 years, unable to use a mouthpiece.

A DPI is a breath-actuated device that uses a gelatin capsule containing a single dose of medication and a carrier substance to aid in the dispersion of the drug. The capsule is inserted into the device and punctured. The patient's inspiratory flow disperses the dry particles and draws them into the lower airways. In spontaneously breathing patients, this device is appropriate in patients who are able to achieve a certain inspiratory flow, such as equal to or greater than 50 L/min. This will typically correspond to children about 6 years or greater.

A LVN can be used to deliver a dose of medication continuously over a period of time. A LVN is powered by a compressed gas source, and a face mask is typically used as the interface.

The two primary means for delivering aerosolized medication to treat a medical condition is an MDI or a nebulizer. MDI medication (drug) canisters are typically sold by manufacturers with a boot that includes a nozzle, an actuator, and a mouthpiece. Patients can self-administer the MDI medication using the boot alone but the majority of patients have difficulty in synchronizing the actuation of the MDI canister and patient inhalation and improve the delivery and improve the delivery of medication by decreasing oropharyngeal deposition of the aerosol drug.

Many valved chambers of this type are commercially available. Examples of such spacers include but are not limited to those structures disclosed in U.S. Pat. Nos. 4,470,412; 5,012,803; 5,385,140; 4,637,528; 4,641,644; 4,953,545; and U.S. patent application publication No. 2002/0129814. These devices are expensive and may be suitable for chronic conditions that require frequent use of MDI inhalers provided the cost and labor involved in frequent delivery of medication is acceptable to the patient. However, under acute symptoms, such devices may fail to serve the purpose and lead to an inadequate delivery of medication.

Aerosol delivery systems that use standard small volume nebulizers are commonly used in acute conditions as they are cheap and overcome the inhalation difficulties associated with actuation of MDI and synchronization of inhalation by the patient. Nebulizers are fraught with numerous problems as well. The medication dose used is about 10 times of that used with an MDI and hence the increased cost without any added proven clinical benefit. Secondly, the majority of the nebulized medication is wasted during exhalation. Thirdly, the time taken to deliver the medication is several times that of an MDI and the labor cost of respiratory therapist may outweigh the benefits of nebulizers compared with MDIs. Breath actuated nebulizers(s) with reservoir have been designed to overcome the medication waste. An example of this type of device is found in U.S. Pat. No. 5,752,502. However, these devices are expensive and still have all the other problems associated with nebulizer use alone. Other examples of aerosol inhalation devices can be found in U.S. Pat. No. 4,210,155, in which there is a fixed volume mist accumulation chamber for use in combination with a nebulizer and a TEE connection.

Problems with prior art devices include that the devices significantly waste medication, they provide a non-uniform concentration of delivered medication, they are expensive, and they are difficult to use. Many of these devices are commercially available in which the nebulizer is directly attached to the TEE connector without any mixing chamber. All of the aforementioned devices can be used with either an MDI or a nebulizer but not both, and hence, face the difficulty associated with either system alone. Other devices have tried to overcome the above problems by incorporating a mixing chamber in the device with adaptability to be used with an MDI or standard nebulizer. U.S. patent application publication No. 2002/0121275 disclosed a device having the above characteristics. However, this device is plagued with problems that are typical to those type of devices. As with other conventional devices, the disclosed device, like the other ones, fails to incorporate some of the key features necessary for enhanced aerosol delivery.

In general, each of the prior art devices suffers from the following deficiencies: (1) the entrained airflow in the device interferes with the MDI plume as well as the plume generated by a nebulizer resulting in increased impaction losses of aerosol generated by either an MDI or nebulizer; (2) the device does not have the ability to deliver a desired precise fraction of inspired oxygen to a hypoxic patient and simultaneously deliver aerosol medication with either a metered dose inhaler (MDI) or a nebulizer; (3) the device can not deliver a gas with a desired density to improve aerosol delivery and a desired fraction of inspired oxygen to a hypoxemic patient; (4) the device does not have the ability to deliver different density gases with a desired fraction of inspired oxygen simultaneously while retaining the ability to deliver aerosol medication at the same time with either an MDI or a nebulizer; (5) the device does not have the ability to deliver a mixture of multiple gases to a patient and simultaneously maintain a desired fraction of inspired oxygen; (6) the device does not serve as a facemask for delivering varying concentrations of inspired oxygen from room air to 100% but serves solely as an aerosol delivery device; (7) the device does not have a reservoir chamber—either as a bag or as a large volume tubing to store nebulized medication that is otherwise wasted during exhalation (The holding chamber of this type of device varies from 90 cc to 140 cc and is not enough to serve as a reservoir for the volume of nebulized medication generated during exhalation is wasted); (8) there is no mechanism in the device to prevent entrainment of room air which forms the bulk of volume during inhalation (the fraction of inspired oxygen and the density of the gas mixture inhaled by the patient may vary with every breath with the device depending on the volume of entrained room air which may vary with each breath); (9) the device does not have any valve system to prevent exhaled carbon dioxide from entering the holding chamber—rebreathing of carbon dioxide from the holding chamber on subsequent inhalation can be extremely detrimental to a patient and extremely dangerous under certain clinical conditions; (10) the device does not have the capability of delivering medication with an MDI and a nebulizer simultaneously; and (11) the device has a fixed volume-holding chamber, which makes the device extremely large and cumbersome to deliver medication.

What is needed in the art and has heretofore not been available is a system that overcomes the above deficiencies and incorporates functionality to make the device a compact, user friendly, economical, and multipurpose aerosol device for both acute and chronic use with either an MDI or a nebulizer or with both devices simultaneously as warranted by the patient's clinical circumstances.

SUMMARY

According to one aspect of the present invention, an accessory for an aerosol inhalation system includes a main conduit body having an outlet end for placement close to a mouth of a patient, and first and second leg conduits in fluid communication with the main conduit body. Each of the first and second leg conduits includes a distal end and the second leg conduit is spaced apart from the first leg conduit.

The accessory includes a first port formed as part of the first leg conduit for attachment to a device that generates aerosol particles as a means for delivering medication to the patient. A second port formed as part of the first leg conduit, while a third port is formed as part of the second leg conduit. The accessory further includes a holding chamber having a first compartment and a second compartment separated from the first compartment, with the first compartment being sealingly and fluidly coupled to the second port and the second compartment being sealingly and fluidly coupled to the third port.

An arrangement of valves is provided such that when the patient exhales, the first leg conduit is sealingly closed off from both the main conduit body and the second leg conduit resulting in the aerosol particles flowing into and being held in the first compartment of the holding chamber. Conversely, when the patient inhales, the first leg conduit is opened to the main conduit body and in fluid communication with the second leg conduit resulting in the aerosol particles delivered through the first port being delivered to the patient.

According to another aspect of the present invention, an aerosol inhalation system includes the above described accessory and further includes at least one device for producing aerosol particles to deliver medication to a patient through a piece of equipment in communication with a respiratory system of the patient. The accessory is in the form of an interface between the at least one device and the piece of equipment and includes (1) a main conduit body having an outlet end connected to the piece of equipment; (2) a first leg conduit in fluid communication with the main conduit body; and (3) a second leg conduit in fluid communication with the main conduit body, with the second leg conduit being spaced apart from the first leg conduit. The accessory also includes a first port formed as part of the first leg conduit for attachment to the at least one device, a second port formed as part of the first leg conduit; and a third port formed as part of the second leg conduit.

The accessory also has a holding chamber defined by a first compartment and a second compartment separated from the first compartment. The first compartment is sealingly and fluidly coupled to the second port and the second compartment is sealingly and fluidly coupled to the third port. Associated with the accessory is an arrangement of valves including a first valve and a second valve. The first valve opens up the first leg conduit to the main conduit body under a first prescribed event and closes the second leg conduit to the main conduit body under a second prescribed event. The second valve is provided for venting the second leg conduit under the second prescribed event.

A supplemental gas source is provided in selective communication with the second compartment for delivering supplemental gas under prescribed conditions. The supplemental gas source includes a third valve for controlling a flow rate of the supplemental gas into the second compartment.

Further aspects and features of the exemplary aerosol inhalation system disclosed herein can be appreciated from the appended Figures and accompanying written description.

BRIEF DESCRIPTION OF THE DRAWING FIGURES

The foregoing and other features of the present invention will be more readily apparent from the following detailed description and drawings of the illustrative embodiments of the invention wherein like reference numbers refer to similar elements and in which.

DETAILED DESCRIPTION OF PREFERRED EMBODIMENTS

Now turning to FIGS. 1-5 in which an accessory or interface element 100 according to one exemplary embodiment and for use in an aerosol delivery system is illustrated. As described below, the accessory 100 is intended for use with a nebulizer or an MDI or another piece of aerosol inhalation equipment. The accessory 100 is defined by a body 110 that can be formed of any number of different materials, including a plastic material or a metal. The accessory 100 is essentially a hollow body 110 that has a first end (inlet end) 112 and an opposing second end (outlet end) 114. The accessory 100 is intended to act as a fluid connector in that it is fluidly attached to another piece of equipment, such as a facemask, that is directly coupled to the patient's mouth, as well as being fluidly attached to an actuatable device that generates the aerosol particles (aerosolized medication) that are delivered to the patient.

Figure 2:
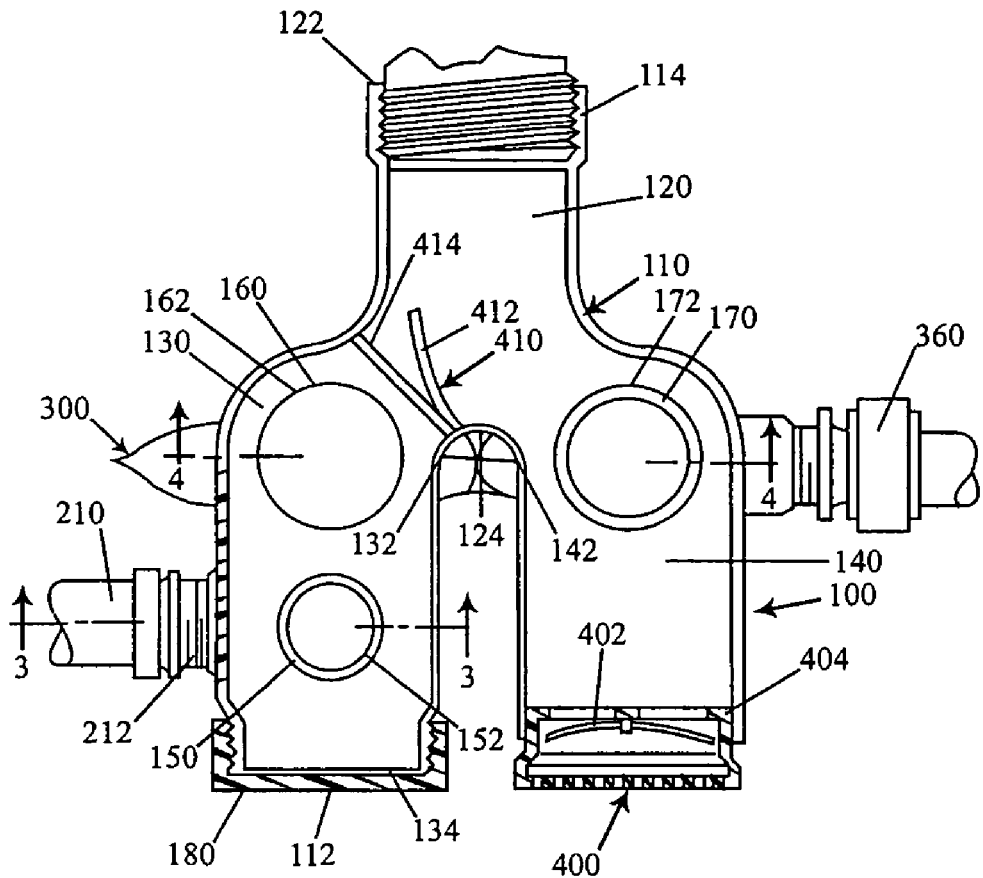
FIG. 2 is a cross-sectional view taken along the line 2-2 of FIG. 1.
Figure 3:
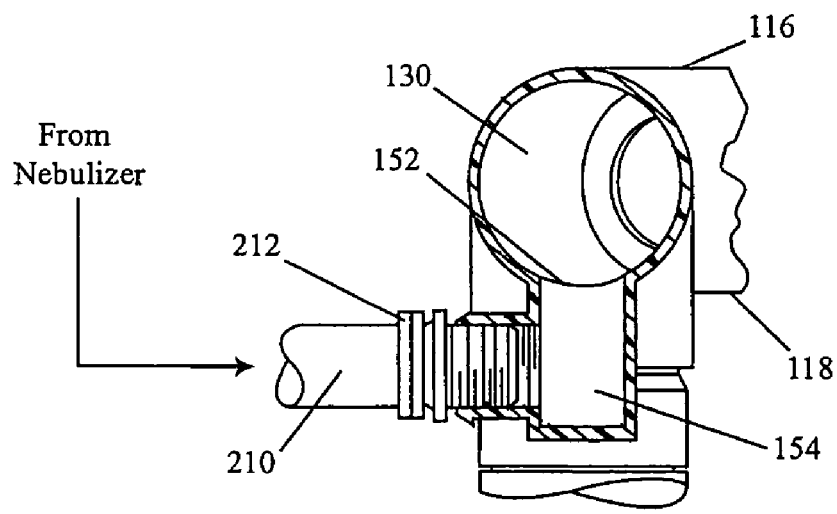
FIG. 3 is a cross-sectional view taken along the line 3-3 of FIG. 2.
Figure 4:
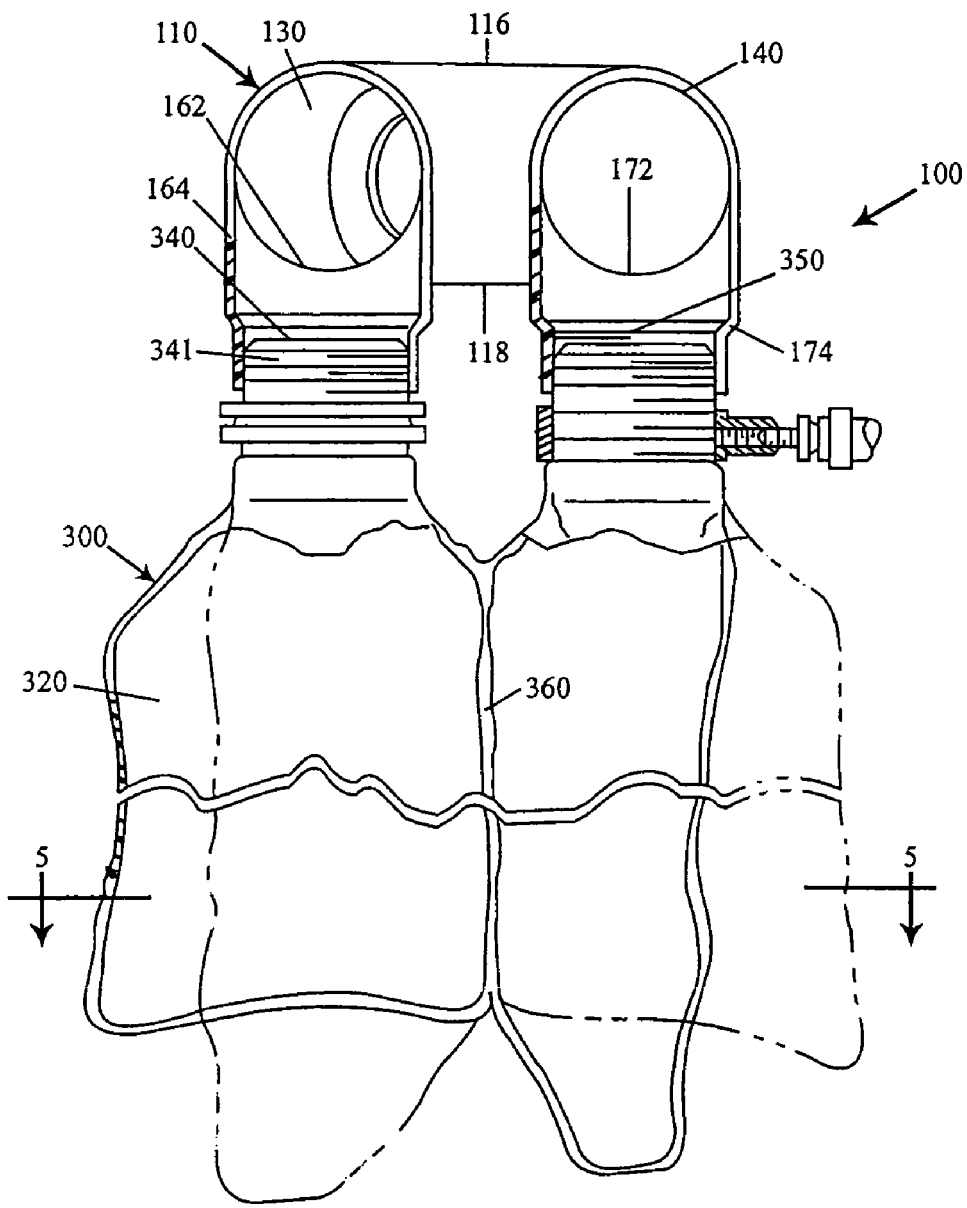
FIG. 4 is a cross-sectional view taken along the line 4-4 of FIG. 2.
Figure 5:
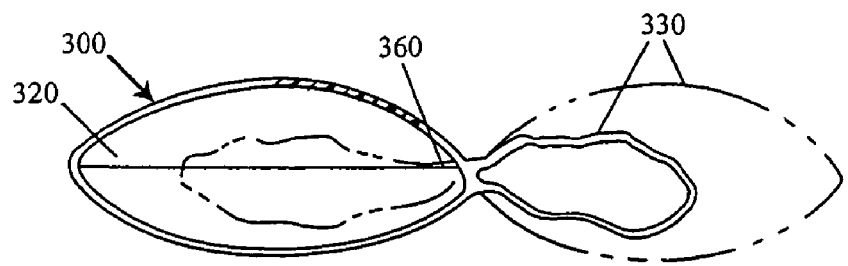
FIG. 5 is a cross-sectional view taken along the line 5-5 of FIG. 4.

In the illustrated embodiment, the accessory 100 is in the form of a tubular Y-shaped connector and therefore the body 110 is defined by a main conduit portion 120 and a first leg conduit 130 and a second leg conduit 140, with the first and second leg conduits 130, 140 being fluidly connected to the main conduit portion 120. FIG. 2 is a cross-sectional view which illustrates the Y-shaped nature of the conduits with the first and second leg conduits 130, 140 being spaced thereapart. The first and second leg conduits 130, 140 are substantially parallel to one another. The body 110 can also be thought of as having an upper or top surface or face 116 and an opposing lower or bottom surface or face 118. In the illustrated embodiment, the accessory body 110 is shown as having a circular cross-section; however, it will be appreciated that the body 110 can have any number of other cross-sectional shapes.

The main conduit portion 120 therefore has an open first end 122 and a second end 124 which interfaces and is fluidly connected to the first and second leg conduits 130, 140. The first leg conduit 130 has a first end 132 that interfaces with the second end 124 and an opposing open second-end 134. The second-leg conduit 140 has a first end 142 that interfaces with the second end 124 and an opposing open second end 144 which is adjacent the open second end 134 of the first leg conduit 130. The main conduit portion 120 is the part of the accessory that is intended to be connected to equipment that is placed over the patient's mouth and in one preferred embodiment, the main conduit portion 120 engages and sealingly couples with a facemask that is intended for placement over the patient's nose and mouth. Thus, the main conduit portion 120 is the principal pathway for fluid, such as air and the aerosol particles, to either enter the patient in the case of the aerosol particles and air or be discharged from the patient as in the case of exhaled gases, such as carbon dioxide.

The body 110 includes a plurality of ports or interface members or regions that permit a part to be fluidly connected to the body 110. In the illustrated embodiment, the body 110 includes three ports formed as a part of the body 110. More specifically, a first port 150 is formed as a part of the first leg conduit 130 and therefore is in fluid communication with an interior of the first leg conduit 130. The first port 150 thus has an opening 152 that defines an entrance into the first leg conduit 130 and typically, includes a stem, boss or the like 154 that defines the opening 152 and permits a member to be sealingly attached to the first leg conduit 130 and in fluid communication with the interior of the first leg conduit 130. Preferably, the first port 150 is formed on the bottom surface or face 118. The first port 150 is located closer to and preferably is proximate to or adjacent the open second end 134 of the first leg conduit 130.

Similarly, the second port 160 is formed as a part of the first leg conduit 130 and therefore is in fluid communication with an interior of the first leg conduit 130. The second port 160 thus has an opening 162 that defines an entrance into the first leg conduit 130 and typically, includes a stem, boss or the like 164 that defines the opening 162 and permits a member to be sealingly attached to the second leg conduit 140 and in fluid communication with the interior of the first leg conduit 130. Preferably, the second port 160 is formed on the bottom surface or face 118. The second port 160 is located closer to and preferably is proximate or adjacent the first end 132 of the first leg conduit 130, with the first port 150 being formed between the second port 160 and the open second end 134.

Unlike the first and second ports 150, 160, a third port 170 is formed as a part of the second leg conduit 140 and therefore is in fluid communication with an interior of the second leg conduit 140. The third port 170 thus has an opening 172 that defines an entrance into the second leg conduit 140 and typically, includes a stem, boss or the like 174 that defines the opening 172 and permits a member to be sealingly attached to the second leg conduit 140 and in fluid communication with the interior of the second leg conduit 140. Preferably, the third port 170 is formed on the bottom surface or face 118. While the location of the third port 170 is not critical, the illustrated third port 170, which is exemplary in nature, is located closer to and preferably is proximate to or adjacent the first end 142 of the second leg conduit 140. In the illustrated embodiment, the second port 160 and the third port 170 are generally aligned with one another and are essentially spaced apart from one another.

In one particularly preferred embodiment, the accessory 100 is intended for use with a nebulizer, generally indicated at 200, and therefore includes a holding chamber 300 into which the aerosol particles can be stored prior to the patient inhaling. The holding chamber 300 is preferably formed as a member that is collapsible and expandable depending upon whether gas is being delivered thereto or being evacuated therefrom. The holding chamber 300 thus can have a number of different structures that have a variable dimension, such as a variable length or a variable width. In one embodiment, the holding chamber 300 is defined by a bellows-type structure that can either expand or collapse/constrict depending upon the force applied. As with other accessories of this type, the holding chamber 300 is intended to receive and store the aerosol particles prior to the patient inhaling them by means of the accessory 100 and the facemask.

Figure 1:
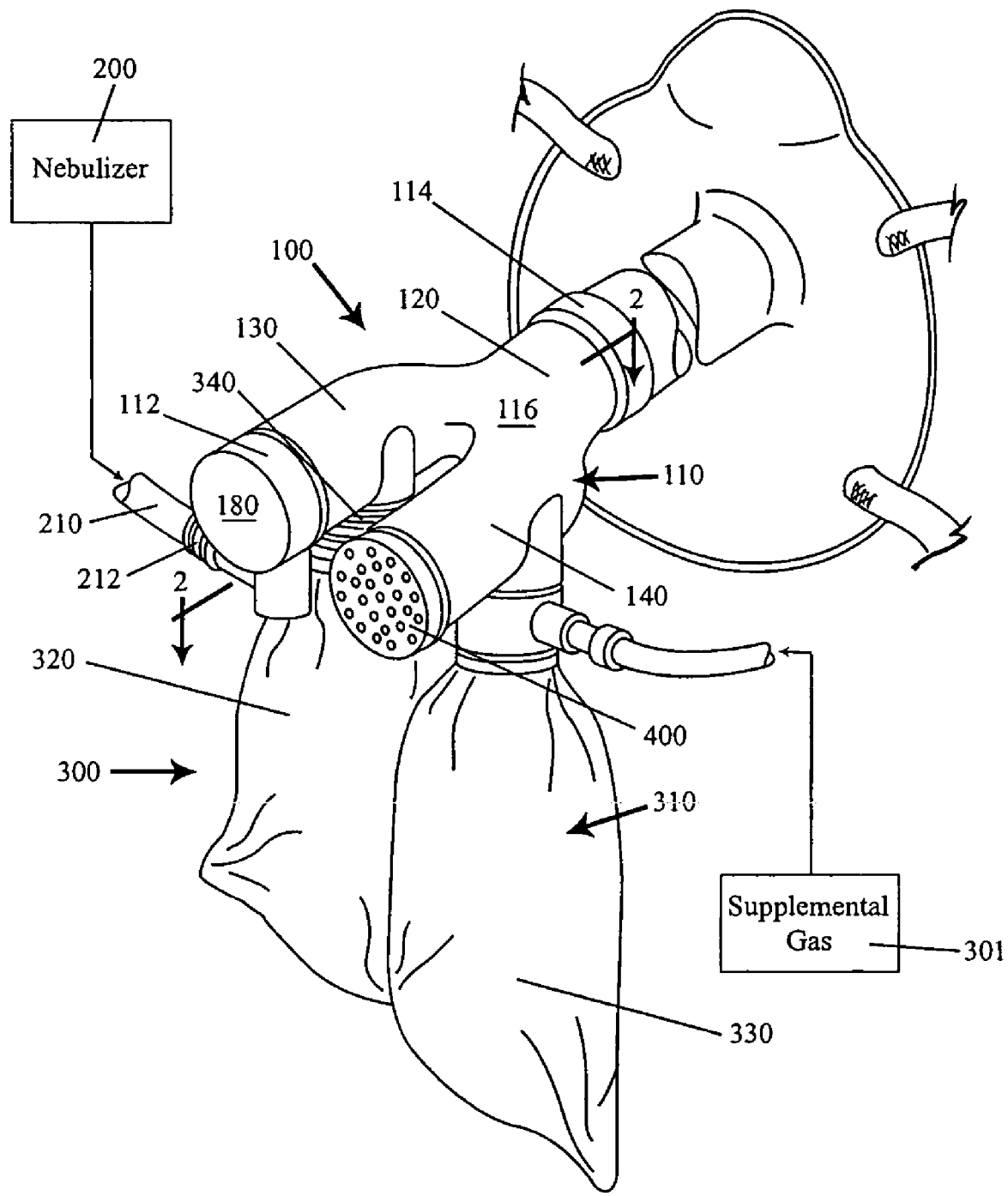
FIG. 1 is a side perspective view of an accessory for use in an aerosol inhalation system according to a first embodiment.

In the illustrated embodiment, the holding chamber 300 is in the form of an expandable/collapsible bag (reservoir bag). According to one aspect of the present invention, the holding chamber 300 is in the form of a bi-furcated bag or the like 310 as shown in FIG. 1. More specifically, the bag 310 is bi-furcated and has two independent distinct compartments, namely a first compartment 320 and a second compartment 330. Since the two compartments 320, 330 are distinct from one another (no fluid communication therebetween), the bag 310 has a first port 340 that forms an entrance and is in fluid communication with the first compartment 320, as well as a second port 350 that forms an entrance and is in fluid communication the second compartment 330. A separating wall or membrane 360 is formed as part of the bag 310 and serves to divide the bag 310 into the first and second compartments 320, 330. The body of the bag 310, as well as the separating wall 360, is preferable formed of a flexible material, such as a fabric that permits the bag 310 to either expand as when fluid enters the bag 310 or contract (collapse) as when the fluid is evacuated from the bag 310. The first port 340 is formed on one side of the separating wall 360, while the second port 350 is formed on the other side of the separating wall 360. Similar to the third port 170 and complementary thereof, the second port 350 is typically defined by a hollow stem or boss 352.

The first port 340 includes a complementary fastening feature 341 that permits it to be sealingly attached to the second port 150 of the first leg conduit 130, and similarly, the second port 350 includes a complementary fastening feature 351 that permits it to be sealingly attached to the third port 170 of the second leg conduit 140. For example, the first and second fastening features 341, 351 can be in the form of threads that mate with complementary threads that are part of the second and third ports 150, 170, respectively. Other fastening means, such as locking means, can likewise be used so long as the accessory 100, and in particular, the first and second leg conduits 130, 140, is sealingly attached to the bag 310. While, the fastening features 341, 351 have been shown as being threads, it will be appreciated that in many applications and embodiments, the third port 170 and second port 350 simply mate with one another via a frictional interface fit where the stem 352 is simply inserted into the stem 174 or vice versa.

In one embodiment, one of the first and second compartments 320, 330 is associated with the nebulizer 200 and more particularly, serves as a holding chamber for the nebulized medication that is generated by the nebulizer 200. The other of the compartments 320, 330 is associated with a supplemental gas source and serves as a supplemental gas holding chamber that supplements the nebulized medication when needed as explained in detail below.

While the two compartments 320, 330 of the bag 310 are illustrated as having equal or about equal volumes, it will be appreciated that the bag 310 can be constructed so that one of the compartments 320, 330 has a greater volume. For example, the first compartment 320 that serves as the nebulizer holding compartment can have a greater volume than the second compartment 330 which receives the supplemental gas to backup the nebulized medication holding chamber.

When the accessory 100 is used with nebulizer 200, the open second end 134 of the first leg conduit 130 is typically closed off or capped by a cap member 180 or the like. The cap 180 is sealingly received in the open second end 134 and serves to seal the first leg conduit 130; however, the cap 180 is preferably a removeable member.

The accessory 100 includes a number of different valve assemblies that are positioned within the body 110. More specifically, a first valve assembly 400 is disposed within the open second end 144 of the second leg conduit 140 and in the illustrated embodiment, the first valve assembly 400 functions as an exhalation valve. The first valve assembly 400 includes a valve element 402 which is positionable between an open position and a closed position and which can be any number of different type of valve structures so longer as they function in the intended manner and provide the desired results. The valve 402 typically seats against a valve seat 404 that is formed at the second end 144 when the valve 402 is closed. The illustrated valve 402 is a one-way flap valve that presses against the valve seat 404 on inhalation and completely occludes the open second end 144 to prevent any room air entrainment (i.e., not allowing the air from the atmosphere to enter into the second leg conduit 140 on inhalation). On exhalation, the flap valve 402 moves away from the flap valve seat 404 for the air exhaled by the patient to escape into the atmosphere from the main conduit portion 120 by flowing through the second leg conduit 140 and then through the opening formed at the second end 144. The open second end 144 is the only means for the exhaled air to escape as will be appreciated below since the three ports 150, 160, 170 are capped or otherwise not open and the second end 144 of the first leg conduit 130 is also capped or otherwise closed.

A second valve assembly 410 is provided and functions as an inhalation valve in that the valve moves between an open position and a closed position depending upon whether the patient is inhaling or exhaling. The second valve assembly 410 is disposed within the body 110 and in particular, the second valve assembly 410 is disposed at an interface between the first leg conduit 130 and the main conduit portion 120 such that when the second valve assembly 410 is in an open position, fluid can flow between the main conduit portion 120 and the first leg conduit 130, while in a closed position, fluid is prevented from flowing therebetween. In other words, the second valve assembly 410 is disposed at the first end 132 of the first leg conduit 130. The second valve assembly 410 includes a valve element 412 and typically and as with the first valve assembly 400, the second valve assembly 410 includes a valve seat 414 against which the valve 412 seals in the closed position.

The second valve element 412 can be any number of different one-way valves and in one embodiment, the second valve element 412 is a flap valve that opens upon inhalation and conversely, closes upon exhalation. The second valve element 412 extends completely across the conduit/passageway of the first leg conduit 130 and therefore, this valve 412 serves to completely close off the first leg conduit 130 from the main conduit portion 120.

The second valve element 412 is located such that both the first and second ports 150, 160 are located between the second valve 412 and the second end 134 and therefore, these ports 150, 160 are completely closed off from the main conduit portion 120 when the second valve element 412 is in the closed position.

In the illustrated embodiment, all three of the ports 150, 160, 170 are located on the bottom face 118 of the body 110. The first port 150 is intended to be fluidly attached to the device that generates the aerosol particles (medication) that is delivered to the patient and preferably, as illustrated, the first port 150 is fluidly connected to the nebulizer 200. More specifically, a connector 212 of a conduit (tube) 210 of the nebulizer 200 is sealingly attached to the first port 150 so that the nebulized medication is delivered through the conduit 210 and into the interior of the first leg conduit 130 and when the second valve element 412 is open, the nebulized medication (aerosol particles) travel the length of the first leg conduit 130 through the opening defined by the valve seat 414 and into the main conduit portion 120 and then into the equipment (facemask) that delivers the medication to the patient. This is the sequence of events when the patient inhales. Conversely, when the patient exhales, the second valve element 412 closes; however, the nebulizer 200 continues to deliver the nebulized medication through the first port 150 into the interior of the first leg conduit 130. Since the second valve element 412 is closed when the patient exhales prior to the next inhalation, the nebulized medication can not flow into the main conduit portion 120 but instead flows through the second port 160 through the first port 340 and into the first compartment 320 of the bag 310.

The interface between the nebulizer 200 and the first port 150 does not have to be a threaded one as illustrated; but instead, can be any number of types of interfaces. One preferred interface between the nebulizer 200 and the first port 150 is merely a frictional fit interface where one of the nebulizer stem and the body (stem) of the first port 152 is inserted into the other one.

The first compartment 320 of the bag 310 is therefore intended to act as a main reservoir bag in that the first compartment 320 receives and holds the nebulized medication until the patient inhales. The first compartment 320 of the bag 310 thus expands until the patient inhales at which time the second valve element 412 opens and the inhalation of the patient draws the nebulized medication out of the first compartment 320 into the first conduit leg 130 then into the main conduit body 120 where it is delivered to the patient. In FIGS. 4 and 5, the solid lines show the first and second compartments 320, 330 in a condition where only the first compartment 320 is significantly expanded.

There are some circumstances where an insufficient amount of nebulized medication is present in the first compartment 320 of the bag 310. This may result because the flow rate of the nebulizer 200 is insufficient for the patient as when the patient has a greater body weight than the flow rate setting of the nebulizer 200. When this does occur, the patient experiences a very uncomfortable feeling in that the patient will experience an insufficient air flow to the lungs and therefore will begin to breathe more deeply and rapidly. In other words, the patient may begin feeling as though they need to gasp for air to breathe.

The present invention overcomes such potential deficiency in air flow to the patient by providing the second compartment 330 in the bag 310 which acts as a supplemental air source for the patient due to the second compartment 330 being attached to a supplemental gas source, generally indicated at 301. Preferably, the gas source 301 connects to the stem 352 of the second port 350 as shown in the figures; however, it is possible for the gas source 301 to be directly connected to the second compartment 330 of the bag 310. In any event, the gas source 301 is directly and fluidly connected to the second compartment 330 and therefore, the gas is delivered into the second compartment 330. As with the flow of nebulized medication into the first compartment 320, the flow of the gas source 301 into the second compartment 330 causes the second compartment 330 to expand as the bag 310 is filled with gas. This shown in FIGS. 4 and 5 by the phantom lines which show both the first and second compartments 320, 330 significantly expanded.

It will be appreciated that the gas source 301 serves as a supplemental gas since gas stored in the second compartment 330 is in selective fluid communication with the main conduit member 120 and therefore, can flow to the patient under certain circumstances as discussed-below. In other words, if there is insufficient gas in the form of nebulized gas in the first compartment, when the patient inhales, then the patient will not experience the above described breathing problems since the second compartment 330 is open to the patient through the main conduit portion 120 and therefore, the patient can inhale the supplemental gas that is present in the second compartment 330 to make up for any shortfall in gas in the first compartment 320.

The gas source 301 typically has an associated valve assembly (not shown) that is external to the system 100 and is typically at the gas source 301 for controlling the flow rate of the gas source 301 into the second compartment 330. The valve assembly is preferably an adjustable valve that controls the flow rate of the supplemental gas into the second compartment 330. Any number of different valve mechanisms are suitable for this type of application and typically include an adjustable part, such as a dial, that permits the physician to easily alter and change the flow characteristics. For example, the valve mechanism can include an adjustable member that when manipulated either sequentially closes or opens the opening formed in the conduit that delivers the supplemental gas to the second compartment 330.

Thus, the physician can initially set the valve at one setting which the physician believes will provide a sufficient supplemental gas flow into the second compartment 330 based on the physician's past experiences and based on certain characteristics of the patient, such as the size and weight of the patient. For example, when the patient is a large adult or even a large child, the flow rate of the nebulized medication into the first compartment 320, even when it is set at a maximum flow rate, may not be sufficient and therefore, this could result in the patient receiving a low level of air and feeling the above noted discomfort. The gas source 301 thus supplements the gas flow of the nebulizer 200 and makes up for any deficiency so that the patient breaths smoothly thoughout the procedure.

When setting the valve, the physician will keep in mind that it may not be desirable to set the flow rate of the supplemental gas at too high a value since this will result in the second bag compartment 320 expanding and also, results in the supplemental gas source 301 mixing with the nebulized medication as the patient inhales, thereby causing a decrease in the inhaled concentration of the medication. As mentioned before, it is desirable to try to keep as fixed as possible the concentration of the inhaled medication. Since the second compartment 330 is fluidly connected to the second leg conduit 140 and the first valve assembly 400, any excess build up of supplemental gas in the second compartment 330 can be vented through the first valve 402 each time the patient exhales.

In the event that the initial setting of the valve is not optimal in that the too much supplemental gas is being delivered to the second bag compartment 330 or too little supplemental gas is being delivered to the second bag compartment 330, the physician simply needs to make the necessary adjustment to the valve to either immediately reduce or increase, respectively, the supplemental gas flow into the second compartment 330. This can be done by simply turning or otherwise manipulating the valve. It is also very easy for the physician to determine whether the flow rate of the supplemental gas source 301 is optimal since the physician can observe the bag 310 and more particularly, can observe whether either the first compartment 320, the second compartment 330 or both compartments 320, 330 appear to be excessively collapsed (thus indicating an increase in flow rate is needed) or excessively expanded or extended (thus indicating a decrease in flow rate is needed). The physician can simply and immediately alter the flow rate and thus, the accessory 100 is tailored to be used with a whole range of different types of patients, from small infants up to large adults.

A supplemental gas valve assembly 360 is provided for controlling the flow of the supplemental gas out of the second compartment 330 and into the second leg conduit 140 and more particularly, to permit flow of the supplemental gas from the second compartment 330 into the second leg conduit 140, through the main conduit member 120 and ultimately to the patient when the patient inhales and conversely, preventing the flow of supplemental gas from the second compartment 330 into the second leg conduit when the patient exhales. It will also be appreciated that when valve assembly 360 closes during exhalation, the exhaled air that includes waste gases is not permitted to flow into the secondary compartment 330 where it could then be drawn into the patient at the next inhalation movement of the patient.

In order to accomplish this, the valve assembly 360 must be located above (upstream) of the incoming supplemental gas source 301. Thus and according to one exemplary embodiment, the valve assembly 360 is positioned within the stem 352 above the location where the second gas source 301 is connected to the stem 352. It will also be appreciated that another location for the valve assembly 360 is in the stem 174 of the third port 170. In either embodiment, the location of the valve assembly 360 can not interfere with the fastening or securing of the stem 352 to the stem 174. Thus, when a frictional fit is the interface means for connecting the stems 352, 174, the valve assembly 360 must be disposed in the stem that has the smaller outer diameter and which is disposed within the larger diameter stem.

The valve assembly 360 moves between an open position and a closed position depending upon whether the patient is inhaling or exhaling. When the valve assembly 360 is in an open position, fluid can flow between the second compartment 330 and the second leg conduit 140, while in a closed position, fluid is prevented from flowing therebetween. The valve assembly 360 includes a valve element 362 and typically and as with the valve assemblies 400, 410, the valve assembly 360 includes a valve seat against which the valve 362 seals in the closed position.

The valve element 362 can be any number of different one-way valves and in one embodiment, the valve element 362 is a flap valve that opens upon inhalation and conversely, closes upon exhalation. The illustrated valve element 362 extends completely across the conduit/passageway of the stem 352 above the entrance location of the gas source 301 and therefore, this valve element 362 serves to completely close off the second compartment 330 from the second leg conduit 140 and the main conduit portion 120 under select conditions, such as exhalation of the patient.

The above described accessory and variations thereof can be used in conventional inhalation equipment settings and thus can be used with conventional nebulizers to overcome the deficiencies that are associated with the prior art aerosol inhalation systems. In addition, the use of a supplemental gas source ensures that the accessory and the disclosed aerosol inhalation system is suitable for use with all types of patients from small infants to large adults irregardless of whether the flow rate of the nebulizer by itself is sufficient to support a normal breathing pattern of the patient.

Now turning to FIGS. 6 and 8-10 in which an accessory or interface element 500 according to one exemplary embodiment and for use in an aerosol delivery system is illustrated. As described below, the accessory 500 is intended for use with a nebulizer or an MDI or another piece of aerosol inhalation equipment. The accessory 500 is defined by a body 510 that can be formed of any number of different materials, including a plastic material or a metal. The accessory 500 is essentially a hollow body 510 that has a first end (inlet end) 512 and an opposing second end (outlet end) 514. The accessory 500 is intended to act as a fluid connector in that it is fluidly attached to another piece of equipment, such as a facemask, that is directly coupled to the patient's mouth, as well as being fluidly attached to an actuatable device that generates the aerosol particles (aerosolized medication) that are delivered to the patient.

In the illustrated embodiment, the body 510 has a main section 516 that includes a number of arms or feet that extend outwardly therefrom, with the inlet end 512 being formed at the end of a first leg 520 that is formed at a right angle to the main section 516. The main section 516 includes a second leg 530 that extends outwardly therefrom between the first leg 520 and the outlet end 514 and a third leg 540 that is located between the outlet end 514 and the second leg 530. The third leg 540 is located proximate the outlet end 514, while the second leg 530 is closer to the first leg 520. The first, second and third legs 520, 530, 540 are thus tubular structures that are in fluid communication with the interior of the tubular main section 516 and are open at their opposite distal ends to receive an object (such as a conduit or connector) or a fluid, etc.

The main section 516 includes a fourth leg 550 that extends outwardly from the main section 516 and is in fluid communication with the interior of the main section 516. Like the other legs, the fourth leg 550 is a tubular structure that is open at its distal end for an attachment to an object (conduit). In the illustrated embodiment, the first, second and third legs 520, 530, 540 extend outwardly from an underside of the tubular main section 516, while the fourth leg 550 extends outwardly from the opposite top side of the tubular main section 516. The fourth leg 550 is located between the second and third legs 530, 540.

The main section 516 is the part of the accessory 500 that is intended to be connected to equipment that is placed over the patient's nose and mouth. Thus, the main section 516 (main conduit) is the principal pathway for fluid, such as air and the aerosol particles, to either enter the patient in the case of aerosol particles and air or to be discharged from the patient as in the case of exhaled gases, such as carbon dioxide.

The first leg 520 serves as a port or connector for mating with a device 200 that generates a gas flow that is intended to be breathed in by the patient. For example, the device 200 can be in the form of a nebulizer or even an MDI or the like. In the illustrated embodiment, the device is in the form of a nebulizer 200 that is fluidly connected to a gas source via a nebulizer conduit 215. The nebulizer 200 is fluidly and sealingly connected to the first leg 520 so that the gas and aerosolized particles generated by the nebulizer 200 are delivered into the interior of the main section 516 of the accessory 500. Any number of techniques can be used to couple the nebulizer 200 to the first leg 520, such as threadingly, snap-fittingly, frictionally, etc., the two together.

In one embodiment, the accessory 500 is intended for use with a nebulizer, generally indicated at 200, and therefore includes a holding chamber 700 into which the aerosol particles can be stored prior to the patient inhaling. The holding chamber 700 is preferably formed as a member that is collapsible and expandable depending upon whether gas is being delivered thereto or being evacuated therefrom. The holding chamber 700 thus can have a number of different structures that have a variable dimension, such as a variable length or a variable width. In one embodiment, the holding chamber 700 is defined by a bellows-type structure that can either expand or collapse/constrict depending upon the force applied. As with other accessories of this type, the holding chamber 700 is intended to receive and store the aerosol particles prior to the patient inhaling them by means of the accessory 500 and the facemask.

Figure 6:
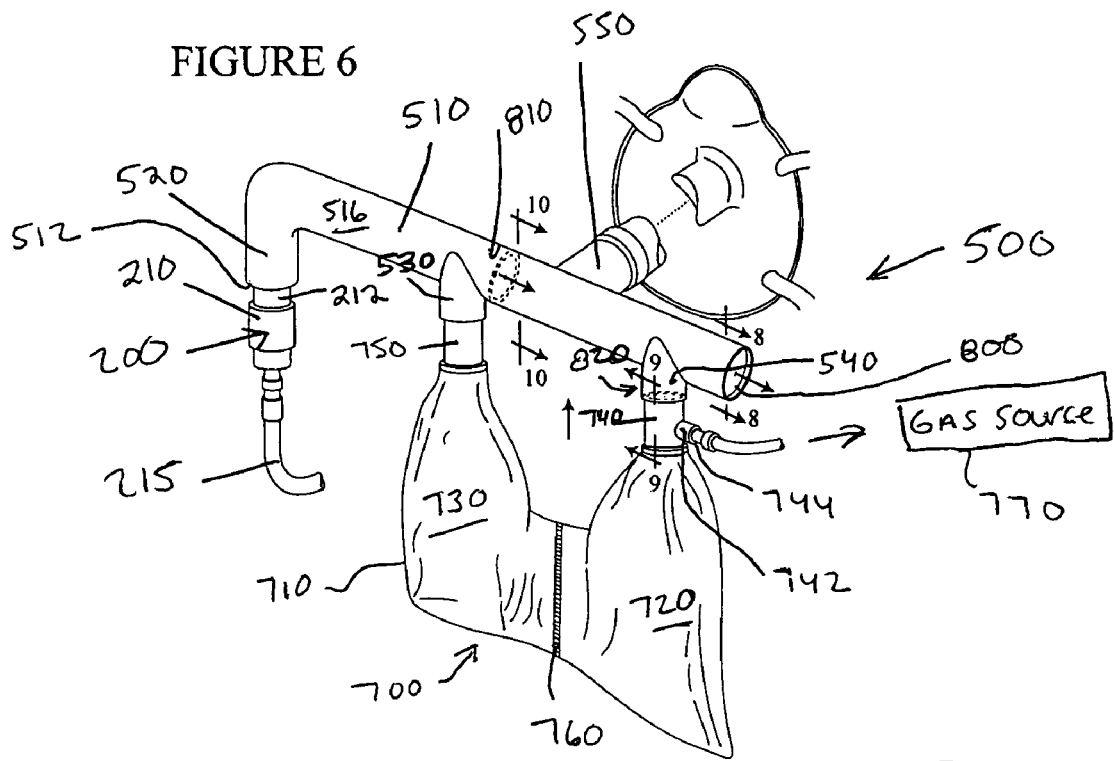
FIG. 6 is a perspective view of an accessory for use in an aerosol inhalation system according to a second embodiment.

In the illustrated embodiment, the holding chamber 700 is in the form of an expandable/collapsible bag (reservoir bag) or similar type structure. According to one aspect of the present invention, the holding chamber 700 is in the form of a bi-furcated bag or the like 710 as shown in FIG. 6. More specifically, the bag 710 is bi-furcated and has two independent distinct compartments, namely a first compartment 720 and a second compartment 730. Since the two compartments 720, 730 are distinct from one another (no fluid communication therebetween), the bag 710 has a first port 740 that forms an entrance and is in fluid communication with the first compartment 720, as well as a second port 750 that forms an entrance and is in fluid communication the second compartment 730. A separating wall or membrane 760 is formed as part of the bag 710 and serves to divide the bag 710 into the first and second compartments 720, 730. The body of the bag 710, as well as the separating wall 760, is preferable formed of a flexible material, such as a fabric that permits the bag 710 to either expand as when fluid enters the bag 710 or contract (collapse) as when the fluid is evacuated from the bag 710. The first port 740 is formed on one side of the separating wall 760, while the second port 750 is formed on the other side of the separating wall 760. Both the first and second ports 740, 750 are typically defined by a hollow stem or boss.

The first port 740 includes a complementary fastening feature that permits it to be sealingly attached to the third leg 540 of the accessory 500, and similarly, the second port 750 includes a complementary fastening feature that permits it to be sealingly attached to the second leg 530. For example, the first and second fastening features can be in the form of threads that mate with complementary threads that are part of the legs 540, 530, respectively. Other fastening means, such as locking means or mechanical fits, such as a frictional fit, can likewise be used so long as the accessory 500, and in particular, the second and third legs 530, 540, are sealingly attached to the bag 710. While, the fastening features can be in the form of threads, it will be appreciated that in many applications and embodiments, the third and second legs 540, 530 and the first and second ports 740, 750 simply mate with one another via a frictional interface fit between two complementary stems.

The first port 740 of the bag 710 also preferably includes a gas inlet port 742 that extends outwardly therefrom and is constructed to attach to a gas source 770. More specifically, the gas inlet port 742 is in fluid communication with and provides an entrance into the first port 740 and is in the form of a tubular structure that has a distal end 744. The end 744 is meant to be attached to the gas source 770 by any number of techniques, including using a gas conduit, such as tubing or the like, that extends from the gas source 770 to the gas inlet port 742. The gas source 770 is preferably connected to a control system or regulator or the like that permits the flow rate of the gas source 770 to be carefully controlled and varied by means, such as valve assemblies and the like that are associated therewith (e.g., valve assembly within the gas conduit).

The gas source 770 can hold any number of different types of gases that are intended for inhalation by the patient through the accessory 500.

The accessory 500 includes a number of different valve assemblies that are positioned within the body 510. More specifically, a first valve assembly 800 is disposed within the open second end 514 of the main section 516 and in the illustrated embodiment, the first valve assembly 800 functions as an exhalation valve. The first valve assembly 800 includes a valve element 802 which is positionable between an open position and a closed position and which can be any number of different types of valve structures so longer as they function in the intended manner and provide the desired results. The valve 802 typically seats against a valve seat 804 that is formed at the second end 514 when the valve 802 is closed. The illustrated valve 802 is a one-way flap valve that presses against the valve seat 804 on inhalation and completely occludes the open second end 514 to prevent any room air entrainment (i.e., not allowing the air from the atmosphere to enter into the main section 516 on inhalation). On exhalation, the flap valve 802 moves away from the flap valve seat 804 for the air exhaled by the patient to escape into the atmosphere from the main section 516 by flowing through the fourth leg 550 from a mask or the like and then through the main section 516 and through the opening formed at the second end 504. The open second end 504 is the only means for the exhaled air to escape as will be appreciated below since the four legs 520, 530, 540, 550 are connected to devices, are capped or otherwise not open.

A second valve assembly 810 is provided and functions as an inhalation valve in that the valve moves between an open position and a closed position depending upon whether the patient is inhaling or exhaling. The second valve assembly 810 is disposed within the body 510 and in particular, the second valve assembly 810 is disposed within the main section 516 at a location between the second leg 530 and the fourth leg 550 such that when the second valve assembly 810 is in an open position, fluid can flow from both the first leg 510 and the nebulizer 200, as well as from the second leg 530 and the second compartment 730 of the bag 710, and into the fourth leg 550 where it can flow into the patient's mask and into the patient's respiratory system.

The second valve assembly 810 includes a valve element 812 that can be any number of different types of valve structures so long as they function in the intended manner and provide the desired results. The valve 812 typically seats against a valve seat 814 that is formed within the main section 516 when the valve 812 is closed. The illustrated valve 812 is a one-way flap valve that presses against the valve seat 814 on exhalation and completely occludes the main section 516 to prevent any exhaled air to flow from the mask and fourth leg 550 and into either the second compartment 730 of the bag 710 or the first leg 520. On inhalation, the flap valve 812 moves away from the flap valve seat 814 to permit the gas from the nebulizer 200 and/or gas stored in the second compartment 730 of the bag 710 to flow into and through the main section 516 and into the fourth leg 550 where it flows into the mask to the patient.

A third valve assembly 820 is provided and is disposed in the third leg 540 or it can be provided in the stem that defines the first port 740 that is associated with the bag 710. The third valve assembly 820 functions as an inhalation valve in that the valve moves between an open position and a closed position depending upon whether the patient is inhaling or exhaling.

The third valve assembly 820 includes a valve element 822 that can be any number of different types of valve structures so long as they function in the intended manner and provide the desired results. The valve 822 typically seats against a valve seat 824 that is formed within either the third leg 540 or first port 740 when the valve 822 is closed. The illustrated valve 822 is a one-way flap valve that presses against the valve seat 824 on exhalation and completely occludes the third leg 540 or first port 740 to prevent any exhaled air to flow from the mask and fourth leg 550 and into either the first compartment 720 of the bag 710. On inhalation, the flap valve 822 moves away from the flap valve seat 824 to permit the gas from the first compartment 720 of the bag 710 to flow into and through the main section 516 and into the fourth leg 550 where it flows into the mask to the patient.

While the two compartments 720, 730 of the bag 710 are illustrated as having equal or about equal volumes, it will be appreciated that the bag 710 can be constructed so that one of the compartments 720, 730 has a greater volume. For example, the first compartment 720 that serves as the nebulizer holding compartment can have a greater volume than the second compartment 730 which receives the supplemental gas to backup the nebulized medication holding chamber.

The first leg 520 is intended to be fluidly attached to the device that generates the aerosol particles (medication) that is delivered to the patient and preferably, as illustrated, the first leg 520 is fluidly connected to the nebulizer 200. More specifically, a connector 212 of a conduit (tube) 210 of the nebulizer 200 is sealingly attached to the first leg 520 so that the nebulized medication is delivered through the conduit 210 and into the interior of the first leg 520 and when the second valve element 812 is open, the nebulized medication (aerosol particles) travels the length through the first leg 520 and a portion of the main section 516 and through the opening defined by the valve seat 814 and into the fourth leg 550 and then into the equipment (facemask) that delivers the medication to the patient. This is the sequence of events when the patient inhales. Conversely, when the patient exhales, the second valve element 812 closes; however, the nebulizer 200 continues to deliver the nebulized medication through the first leg 520 into the interior of the main section 516. Since the second valve element 812 is closed when the patient exhales prior to the next inhalation, the nebulized medication can not flow past the valve assembly 810 and into the fourth leg 550 but instead flows through the second leg 530 through the second port 750 and into the second compartment 730 of the bag 710.

The second compartment 730 of the bag 710 is therefore intended to act as a main reservoir bag in that the second compartment 730 receives and holds the nebulized medication until the patient inhales. The second compartment 730 of the bag 710 thus expands until the patient inhales at which time the second valve element 812 opens and the inhalation of the patient draws the nebulized medication out of the second compartment 730 into the main section 516 and then into the fourth leg 550 where it is delivered to the patient.

There are some circumstances where an insufficient amount of nebulized medication is present in the second compartment 730 of the bag 710. This may result because the flow rate of the nebulizer 200 is insufficient for the patient as when the patient has a greater body weight than the flow rate setting of the nebulizer 200. When this does occur, the patient experiences a very uncomfortable feeling in that the patient will experience an insufficient air flow to the lungs and therefore will begin to breathe more deeply and rapidly. In other words, the patient may begin feeling as though they need to gasp for air to breathe.

The present invention overcomes such potential deficiency in air flow to the patient by providing the first compartment 720 in the bag 710 which acts as a supplemental air source for the patient due to the first compartment 720 being attached to a supplemental gas source, generally indicated at 770. Preferably, the gas source 770 connects to the stem of the first port 740 as shown in the figures; however, it is possible for the gas source 770 to be directly connected to the first compartment 720 of the bag 710. In any event, the gas source 770 is directly and fluidly connected to the first compartment 720 and therefore, the gas is delivered into the first compartment 720. As with the flow of nebulized medication into the second compartment 730, the flow of the gas source 770 into the first compartment 720 causes the first compartment 720 to expand as the bag 710 is filled with gas.

It will be appreciated that the gas source 770 serves as a supplemental gas since gas stored in the first compartment 720 is in selective fluid communication with the main section 516 and therefore, can flow to the patient under certain circumstances as discussed below. In other words, if there is insufficient gas in the form of nebulized gas in the second compartment 730, when the patient inhales, then the patient will not experience the above described breathing problems since the first compartment 720 is open to the patient through the main section 516 and therefore, the patient can inhale the supplemental gas that is present in the first compartment 720 to make up for any shortfall in gas in the second compartment 730.

The gas source 770 typically has an associated valve assembly (not shown) that is external to the system and is typically at the gas source 770 for controlling the flow rate of the gas source 770 into the first compartment 720. The valve assembly is preferably an adjustable valve that controls the flow rate of the supplemental gas into the first compartment 720. Any number of different valve mechanisms are suitable for this type of application and typically include an adjustable part, such as a dial, that permits the physician to easily alter and change the flow characteristics. For example, the valve mechanism can include an adjustable member that when manipulated either sequentially closes or opens the opening formed in the conduit that delivers the supplemental gas to the first compartment 720.

Thus, the physician can initially set the valve at one setting which the physician believes will provide a sufficient supplemental gas flow into the first compartment 720 based on the physician's past experiences and based on certain characteristics of the patient, such as the size and weight of the patient. For example, when the patient is a large adult or even a large child, the flow rate of the nebulized medication into the second compartment 730, even when it is set at a maximum flow rate, may not be sufficient and therefore, this could result in the patient receiving a low level of air and feeling the above noted discomfort. The gas source 770 thus supplements the gas flow of the nebulizer 200 and makes up for any deficiency so that the patient breaths smoothly thoughout the procedure.

When setting the valve, the physician will keep in mind that it may not be desirable to set the flow rate of the supplemental gas at too high a value since this will result in the first bag compartment 720 expanding and also, results in the supplemental gas source 770 mixing with the nebulized medication as the patient inhales, thereby causing a decrease in the inhaled concentration of the medication. As mentioned before, it is desirable to try to keep as fixed as possible the concentration of the inhaled medication. Since the first compartment 720 is fluidly connected to the main section 516 via the third leg 540 and is fluidly connected to the first valve assembly 800, any excess build up of supplemental gas in the first compartment 720 can be vented through the first valve 802 each time the patient exhales since the second valve assembly 810 closes when the patient exhales and the supplemental gas can not flow past the second valve assembly 810 toward the other legs and the second compartment 730 of the bag 710.

In the event that the initial setting of the valve is not optimal in that the too much supplemental gas is being delivered to the first bag compartment 720 or too little supplemental gas is being delivered to the first bag compartment 720, the physician simply needs to make the necessary adjustment to the valve to either immediately reduce or increase, respectively, the supplemental gas flow into the first bag compartment 720. This can be done by simply turning or otherwise manipulating the valve. It is also very easy for the physician to determine whether the flow rate of the supplemental gas source 770 is optimal since the physician can observe the bag 710 and more particularly, can observe whether either the first bag compartment 720, the second compartment 730 or both compartments 720, 730 appear to be excessively collapsed (thus indicating an increase in flow rate is needed) or excessively expanded or extended (thus indicating a decrease in flow rate is needed). The physician can simply and immediately alter the flow rate and thus, the accessory 500 is tailored to be used with a whole range of different types of patients, from small infants up to large adults.

A supplemental gas valve assembly is preferably provided for controlling the flow of the supplemental gas out of the first compartment 720 and into the third leg 540 and more particularly, to permit flow of the supplemental gas from the first bag compartment 720 into the third leg 540, through the main section 516 and ultimately to the patient when the patient inhales and conversely, preventing the flow of supplemental gas from the first bag compartment 720 into the third leg 540 when the patient exhales. It will also be appreciated that when valve assembly closes during exhalation, the exhaled air that includes waste gases is not permitted to flow into the first bag compartment 720 where it could then be drawn into the patient at the next inhalation movement of the patient.

Figure 7:
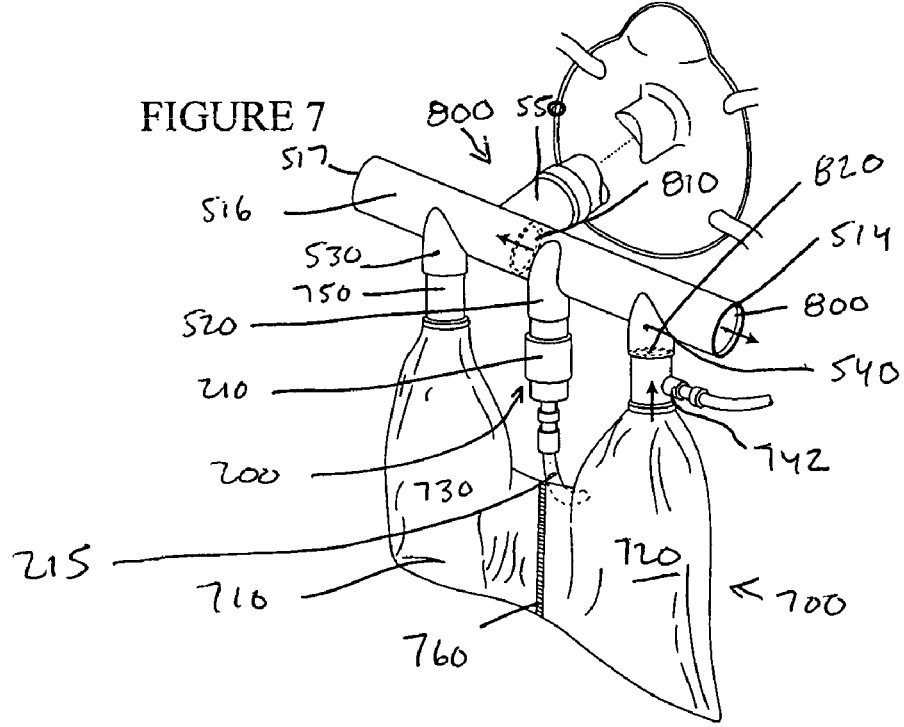
FIG. 7 is a perspective view of an accessory for use in an aerosol inhalation system according to a third embodiment.
Figure 8:
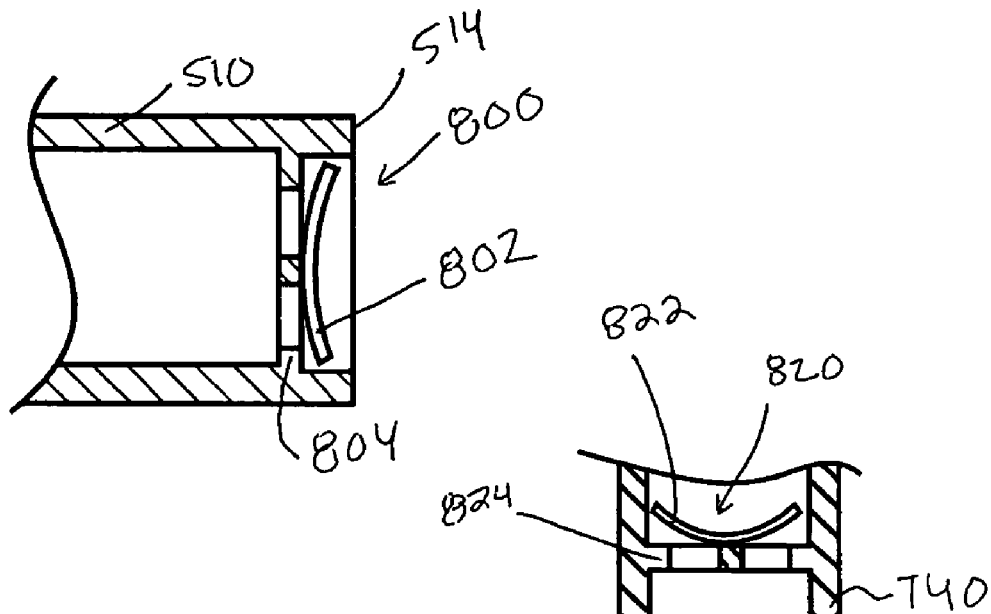
FIG. 8 is a partial cross-sectional view taken along the line 8-8 of FIG. 6.
Figure 9:
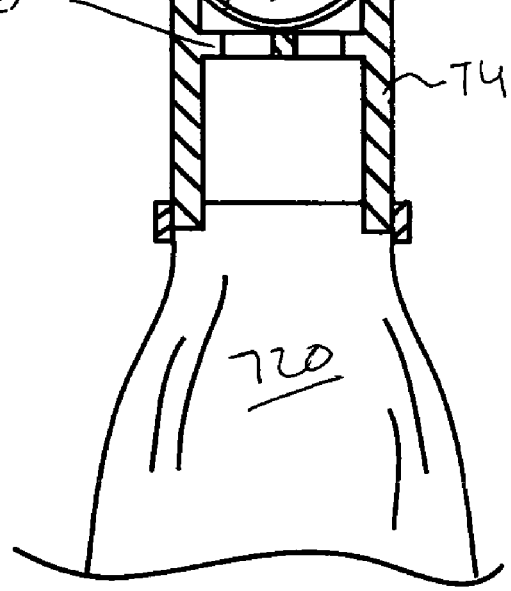
FIG. 9 is a partial cross-sectional view taken along the line 9-9 of FIG. 6.
Figure 10:
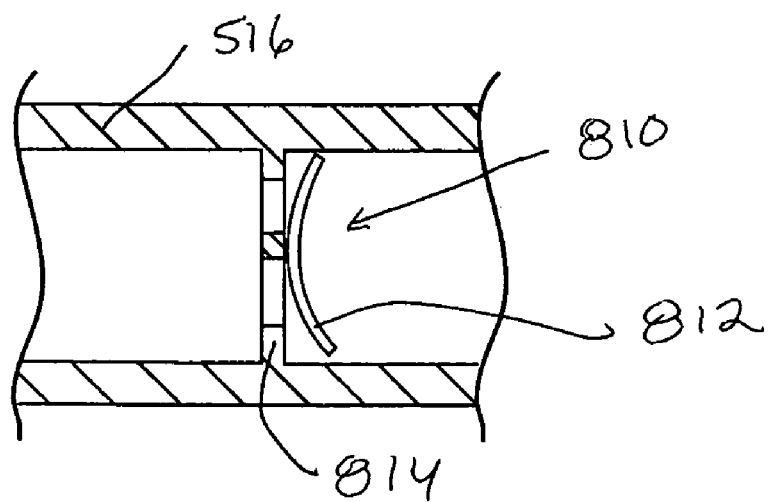
FIG. 10 is a partial cross-sectional view taken along the line 10-10 of FIG. 6.

Now referring to FIG. 7 in which another embodiment of the accessory 800 is illustrated. The accessory 800 is similar to the accessory 500 and therefore, like elements are numbered alike. In the accessory 800, the first leg 520 no longer is formed at one end of the main section 516 but rather is formed in the middle of the main section between the fourth leg 550 and the second leg 530 which is located closer to one end of the main section 516. In this design, the first leg 520 is closer to the fourth leg 550 and since the first leg 520 is still fluidly connected to the nebulizer 200, the length of the gas flow path from the nebulizer 200 to the face mask is less in this embodiment than in the embodiment of FIG. 6 due to the relative positions of the first and fourth legs 520, 550.

Since the first leg 520 is not formed at the end of the main section 516 in this embodiment, the main section 516 has a closed end 517 (e.g., the end 517 can be capped or can the section 515 can be formed so that this is a closed end).

As shown, the first leg 520 is disposed between the second valve assembly 8S-0 and the second leg 530 and in particular, the first leg 520 communicates with the interior of the main section 516 at a location that is near the second valve element 812. It will be appreciated that in this embodiment, the nebulizer 200 is located in front of/downstream from the gas flow from the second compartment 730 of the bag 710 and the present applicants have discovered that the placement of the nebulizer 200 in this location results in improved performance and improved drug delivery since the aerosolized medication is located closer to the face mask as measured along the gas flow path. In addition, this location for the nebulizer 200 permits the gas flow from the second compartment 730 of the bag 710 to assist in carrying the aerosolized medication to the fourth leg 550 and into the patient's mask or the like. In other words, the gas flow from the second compartment 730 acts to entrain the aerosolized medication that is flowing through the first leg 520 from the nebulizer 200.

The operation of the components is the same in this embodiment as in the other embodiments. For example, the valve assemblies 800, 810, 820 operate the same in both embodiments. The first leg 520 is positioned close to the second valve assembly 810 such that once the valve element 812 opens upon inhalation, the gas and aerosolized medication from the nebulizer 200 flows through the valve element 812 and into the fourth leg 550 to the patient.

It will also be appreciated that in each of the embodiments of FIGS. 6 and 7, the first leg 520 can be capped or otherwise sealed as when nebulizer 200 is not used with the respective accessory. In this design, the bag 710 can serve as a means for delivering a gas, such as oxygen or heliox, etc., to the patient. In particular, gas source 770 provides gas the is routed through the first compartment 720 of the bag 710 and into the main section 516 and then into the fourth leg 550 to the face mask.

Having described embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An accessory for an aerosol inhalation system comprising:
 a main conduit body having an outlet end for placement close to a mouth of a patient;
 a first leg conduit in fluid communication with the main conduit body and including a distal end;
 a second leg conduit in fluid communication with the main conduit body and including a distal end, the second leg conduit being spaced apart from the first leg conduit;
 a first port formed as part of the first leg conduit for attachment to a device that generates aerosol particles as a means for delivering medication to the patient;
 a second port formed as part of the first leg conduit; a third port formed as part of the second leg conduit; a holding chamber having a first compartment and a second compartment separated from the first compartment, with the first compartment being sealingly and fluidly coupled to the second port and the second compartment being sealingly and fluidly coupled to the third port; and
 an arrangement of valves such that when the patient exhales, the first leg conduit is sealingly closed off from the main conduit body and the second leg conduit resulting in the aerosol particles flowing into and being held in the first compartment of the holding chamber and conversely, when the patient inhales, the first leg conduit is opened to the main conduit body and in fluid communication with the second leg conduit resulting in the aerosol particles delivered through the first port being delivered to the patient, wherein the holding chamber is defined by a reservoir bag with the first and second compartments defined therein and separated from one another by a bi-furcating wall, the reservoir bag being formed of a expandable/collapsible material, wherein the reservoir bag includes a fourth port integrally formed therewith and fluidly in communication with the first compartment and a fifth port integrally formed therewith and fluidly in communication with the second compartment, each of the fourth and fifth ports including fastening features that permit them to be sealingly mated with the second and third ports.

2. An accessory for an aerosol inhalation system comprising:
a main conduit body having an outlet end for placement close to a mouth of a patient;
a first leg conduit in fluid communication with the main conduit body and including a distal end;
a second leg conduit in fluid communication with the main conduit body and including a distal end, the second leg conduit being spaced apart from the first leg conduit;
a first port formed as part of the first leg conduit for attachment to a device that generates aerosol particles as a means for delivering medication to the patient;
a second port formed as part of the first leg conduit; a third port formed as part of the second leg conduit; a holding chamber having a first compartment and a second compartment separated from the first compartment, with the first compartment being sealingly and fluidly coupled to the second port and the second compartment being sealingly and fluidly coupled to the third port;
an arrangement of valves such that when the patient exhales, the first leg conduit is sealingly closed off from the main conduit body and the second leg conduit resulting in the aerosol particles flowing into and being held in the first compartment of the holding chamber and conversely, when the patient inhales, the first leg conduit is opened to the main conduit body and in fluid communication with the second leg conduit resulting in the aerosol particles delivered through the first port being delivered to the patient; and
a supplemental gas port in fluid communication with the second compartment and for attachment to a supplemental gas source that delivers a prescribed amount of gas to the second compartment to supplement the flow of the aerosol particles through the first port;
wherein the holding chamber is defined by a reservoir bag with the first and second compartments defined therein and separated from one another by a bi-furcating wall, the reservoir bag being formed of a expandable/collapsible material.

3. The accessory of claim 2, wherein the main conduit body, the first leg conduit and the second leg conduit are in the form of a Y-shaped connector.

4. The accessory of claim 2, wherein the first leg conduit and the second leg conduit are substantially parallel to one another and are fluidly joined at the same ends to the main conduit body.

5. The accessory of claim 2, wherein the first, second and third ports are all formed on the same face of the accessory.

6. The accessory of claim 2, wherein the first port is formed closer than the second port to the distal end of the first leg conduit.

7. The accessory of claim 2, wherein the second and third ports are formed the same distance from the distal ends of the first and second leg conduits, respectively.

8. The accessory of claim 2, further including cap sealingly closing off the distal end of the first leg conduit.

9. The accessory of claim 2, wherein the arrangement of valves includes an exhalation valve that is disposed in and seals off the distal end of the second leg conduit, the exhalation valve moving between an open position when the patient exhales, thereby opening the second leg conduit to atmosphere and a closed position when the patient inhales.

10. The accessory of claim 9, wherein the exhalation valve comprises a one way valve.

11. The accessory of claim 2, wherein the arrangement of valves includes an inhalation valve that is disposed in the first leg conduit such that the first and second ports are located between the inhalation valve and the distal end thereof.

12. The accessory of claim 11, wherein the inhalation valve is formed at an interface between the main conduit body and the first leg conduit.

13. The accessory of claim 11, wherein the inhalation valve comprises a one way valve.

14. The accessory of claim 2, wherein the device comprises a nebulizer that delivers the aerosol particles at a prescribed flow rate.

15. The accessory of claim 2, further including a third valve that is associated with one of the fifth port and third port, the third valve moving between an open position when the patient inhales causing the second leg conduit and second compartment to be in fluid communication and a closed position when the patient exhales, thereby fluidly closing off the second compartment from the second leg conduit.

16. The accessory of claim 15, wherein the third valve is a one-way valve and wherein, as the patient inhales, the supplemental gas stored in the second compartment is free to flow through the second leg conduit into the main conduit body to the patient to supplement the aerosol particles flowing through the first leg conduit.

17. The accessory of claim 15, wherein the third valve is formed in the fifth port at a location that is above an inlet of the supplemental gas into the fifth port such that the inlet is between the fifth valve and the second compartment.

18. An aerosol inhalation system comprising:
at least one device for producing aerosol particles for delivering medication to a patient through a piece of equipment in communication with a respiratory system of the patient;
an accessory for interfacing between the at least one device and the piece of equipment, the accessory comprising:
a main conduit body having a first end connected to the piece of equipment and a second end, wherein aerosol particles produced by the device flow into the first end and into the main conduit body toward the second leg, the main conduit body including a patient port that is for placement close to a mouth of a patient for delivering the medication thereto;
a first leg conduit in fluid communication with the main conduit body and including a distal end;
a second leg conduit in fluid communication with the main conduit body and including a distal end, the second leg conduit being spaced apart from the first leg conduit;
a holding chamber having a first compartment and a second compartment separated from the first compartment, with the first compartment being sealingly and fluidly coupled to the first leg and the second compartment being sealingly and fluidly coupled to the second leg; and
an arrangement of valves including a first valve in the form on an inhalation valve that is disposed along the main conduit body between the first and second legs and between the second leg and the patient port, wherein when the first valve opens, a flow path is created between the device that produces the aerosol particles and the patient port and between the second leg and patient to permit the medication to flow freely through the main conduit body to the patient, wherein when the first valve is closed, medication is prevented from flowing from the device to the patient port and from the second leg to the patient port, thereby resulting in the medication being stored in the second compartment which is open to the main conduit body, wherein a second valve is provided for venting the main conduit body when the patient exhales;

wherein the holding chamber is defined by a reservoir bag with the first and second compartments therein and separated from one another by a bi-furcating wall, the reservoir bag being formed of a expandable/collapsible material.

19. The system of claim 18, wherein each of the first and second valves comprises a one-way valve.

20. The system of claim 18, wherein the device comprises a nebulizer that delivers the aerosol particles at a prescribed flow rate.

21. The system of claim 18, wherein during the first prescribed event by the patient, the supplemental gas stored in the second compartment is free to flow through the second leg conduit into the main conduit body to the patient to supplement the aerosol particles flowing through the first leg conduit.

22. The system of claim 18, wherein the third valve is a one way valve that permits the supplemental gas from flowing into the second leg conduit when the patient inhales and prevents the supplemental gas from flowing into the second leg conduit when the patient exhales gas, the exhaled gas being prevented from flowing into the first compartment by means of the first valve and into the second compartment by means of the third valve.

23. The system of claim 18, further including a third valve for controlling flow between the first compartment and the main conduit body, wherein the third valve is an inhalation valve that opens when the patient inhales and closes during exhalation, thereby closing off the first compartment when the patient exhales.

24. The system of claim 23, further including a supplemental gas source in communication with the second compartment, wherein the supplemental gas is permitted to flow into the main conduit body when the third valve is open as a result of inhalation and is prevented to flow into the main conduit body when the third valve is closed as a result of exhalation.

25. The system of claim 18, wherein the second valve is located at the second end of the main conduit body.

26. An accessory for an aerosol inhalation system comprising:
a main conduit body having an outlet port for placement close to a mouth of a patient;
at least a first leg and a second leg each in fluid communication with the main conduit body and located along a longitudinal length of the main conduit body;
a device that generates aerosol particles as a means for delivering medication to the patient through the outlet port, the device being in fluid communication with the main conduit body;
a holding chamber having a first compartment and a second compartment separated from the first compartment, with the first compartment being sealingly and fluidly coupled to the first leg and the second compartment being sealingly and fluidly coupled to the second leg;
a supplemental gas source that is in fluid communication with the first compartment of the holding chamber for delivering supplemental gas thereto; and
an arrangement of valves such that when the patient exhales, the first and second legs are sealingly closed off from the outlet port of the main conduit body resulting in the aerosol particles that enter the main conduit body from the device being directed into and stored within the second compartment until when the patient inhales and a flow path is established between both the device and the outlet port and the second compartment and the outlet port resulting in the aerosol particles being delivered to the patient, wherein the arrangement of valves includes a supplemental gas valve that is located within the first leg and moves between an open position, when the patient inhales, where the supplemental gas flows to the main conduit body and a closed position where the supplemental gas is prevented from flowing into the main conduit body and is stored in the first compartment, the second leg being located along the main conduit body such that the aerosol particles entering the main conduit body can flow to the second compartment without passing though a valve; wherein the holding chamber is defined by a reservoir bag with the first and second compartments therein and separated from one another by a bi-furcating wall, the reservoir bag being formed of a expandable/collapsible material.

27. The accessory of claim 26, wherein the outlet port is located between the first and second legs and between an exhalation valve at one end of the main conduit body and a first inhalation valve located in the main conduit body between the first and second.

* * * * *